United States Patent
Lu et al.

(10) Patent No.: US 11,116,752 B2
(45) Date of Patent: Sep. 14, 2021

(54) PHARMACEUTICAL COMPOSITION COMPRISING BICYCLO-SUBSTITUTED PYRAZOLON AZO DERIVATIVE OR SALT THEREOF AND PREPARATION METHOD THEREOF

(71) Applicant: Jiangsu Hengrui Medicine Co., Ltd., Jiangsu (CN)

(72) Inventors: Yun Lu, Jiangsu (CN); Xinhua Zhang, Jiangsu (CN); Daimei Zhang, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 0 days.

(21) Appl. No.: 16/070,388

(22) PCT Filed: Jan. 16, 2017

(86) PCT No.: PCT/CN2017/071219
§ 371 (c)(1),
(2) Date: Jul. 16, 2018

(87) PCT Pub. No.: WO2017/124983
PCT Pub. Date: Jul. 27, 2017

(65) Prior Publication Data
US 2019/0022065 A1    Jan. 24, 2019

(30) Foreign Application Priority Data

Jan. 22, 2016 (CN) .......................... 201610046767.7

(51) Int. Cl.
| | |
|---|---|
| *A61K 31/4155* | (2006.01) |
| *A61K 47/26* | (2006.01) |
| *A61K 47/38* | (2006.01) |
| *A61K 9/20* | (2006.01) |
| *A61K 9/48* | (2006.01) |
| *A61K 47/36* | (2006.01) |
| *A61P 7/04* | (2006.01) |

(52) U.S. Cl.
CPC ............ *A61K 31/4155* (2013.01); *A61K 9/20* (2013.01); *A61K 9/48* (2013.01); *A61K 47/26* (2013.01); *A61K 47/36* (2013.01); *A61K 47/38* (2013.01); *A61K 9/2095* (2013.01); *A61K 9/4833* (2013.01); *A61P 7/04* (2018.01)

(58) Field of Classification Search
CPC ........ A61K 31/4155; A61K 9/20; A61K 9/48; A61K 47/26; A61K 47/36; A61K 47/38; A61K 9/2095; A61K 9/4833; A61P 7/04
See application file for complete search history.

(56) References Cited

U.S. PATENT DOCUMENTS

2012/0164102 A1* 6/2012 Tang .................... A61P 7/00
424/85.2

FOREIGN PATENT DOCUMENTS

| CN | 101679286 A | 3/2010 | |
|---|---|---|---|
| CN | 102159217 A | 8/2011 | |
| CN | 104844582 A | 8/2015 | |
| WO | 2010142137 A1 | 12/2010 | |
| WO | WO-2010142137 A1 * | 12/2010 | ........... C07D 231/46 |

OTHER PUBLICATIONS

Abdelbary (Year: 2009).*
Kuter et al, "The purification of megapoietin: A physiological regulator of megakaryocyte growth and platelet production," Proceedings of the National Academy of the Sciences of the United States of America, vol. 91, pp. 11104-11108 (Nov. 1994).
Bartley et al, "Identification and Cloning of a Megakaryocyte Growth and Development Factor that is a Ligand for the Cytokine Receptor Mpl," Cell, vol. 77, pp. 1117-1124 (Jul. 1, 1994).
Kaushansky et al, "Promotion of megakaryocyte progenitor expansion and differentiation by the c-Mpl ligand thrombopoietin," Nature, vol. 369, pp. 568-571 (Jun. 16, 1994).
Wendling et al, "c-Mpl ligand is a humoral regulator of megakaryocytopoiesis," Nature, vol. 369, pp. 571-574 (Jun. 16, 1994).
De Sauvage et al, "Stimulation of megakaryocytopoiesis and thrombopoiesis by the c-Mpl ligand," Nature, vol. 369, pp. 533-538 (Jun. 16, 1994).
The second method (paddle method) of the dissolution rate test described in the appendix of vol. II of Chinese Pharmacopoeia 2010 Edition.
Int'l Search Report dated Apr. 21, 2017 in Int'l Application No. PCT/CN2017/071219.

* cited by examiner

*Primary Examiner* — Jeffrey S Lundgren
*Assistant Examiner* — Ibrahim D Bori
(74) *Attorney, Agent, or Firm* — Ice Miller LLP

(57) ABSTRACT

Disclosed is a pharmaceutical composition containing a bicyclo-substituted pyrazolone azo derivative or a salt thereof and a preparation method thereof. In particular, the pharmaceutical composition disclosed in the present invention contains (Z)-5-(2-hydroxyl-3-(2-(3-methyl-5-oxo-1-(5,6,7,8-tetrahydronaphthalene-2-yl)-1H-pyrazol-4(5H)-ylidene)hydrazino)phenyl)furan-2-carboxylic acid or a pharmaceutically acceptable salt thereof, and at least one filler optionally selected from cellulose, microcrystalline cellulose, lactose and starch. The composition has a good stability, dissolution rate and bioavailability, and the preparation process is simple, economical and quick.

14 Claims, 2 Drawing Sheets

PHARMACEUTICAL COMPOSITION COMPRISING BICYCLO-SUBSTITUTED PYRAZOLON AZO DERIVATIVE OR SALT THEREOF AND PREPARATION METHOD THEREOF

CROSS-REFERENCE TO RELATED APPLICATION

This application is a Section 371 of International Application No. PCT/CN2017/071219, filed Jan. 16, 2017, which was published in the Chinese language on Jul. 27, 2017, under International Publication No. WO 2017/124983 A1, which claims priority under 35 U.S.C. § 119(b) to Chinese Application No. 201610046767.7, filed Jan. 22, 2016, the disclosures of which are incorporated herein by reference in their entirety.

FIELD OF THE INVENTION

The present invention belongs to the field of pharmaceutical formulations, and specifically relates to a pharmaceutical composition comprising (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or a pharmaceutically acceptable salt thereof, and at least one filler optionally selected from the group consisting of cellulose, microcrystalline cellulose, lactose and starch. The composition has a good stability, dissolution rate, bioavailability and the like.

BACKGROUND OF THE INVENTION

Thrombopoietin (TPO), also called megakaryocyte growth and development factor (MGDF), is a 332-amino acid glycosylated polypeptide that plays a key role in the regulation of megakaryocytopoiesis and the production of platelets from bone marrow megakaryocytes (Kuter et al., Proc. Nat. Acad. Sci. USA 91: 11104-11108 (1994); Barley et al., Cell 77: 1117-1124 (1994); Kaushansky et al., Nature 369: 568-571 (1994); Wendling et al., Nature 369: 571-574 (1994); and Sauvage et al., Nature 369: 533-538 (1994)).

Platelets are necessary for blood clotting. When platelet count is very low, a patient is at risk of death due to bleeding. Therefore, TPO has been used for the treatment of various blood diseases.

CN101679286A discloses (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid (referred to as compound A hereinafter), the structure of which is shown below. It is a thrombopoietin (TPO) receptor agonist that can increase the production of platelets, and is useful for the treatment of various blood diseases, such as diseases caused by platelet defects. At the same time, it can also be useful for the treatment of thrombocytopenia, especially thrombocytopenic conditions caused by chemotherapy, radiation therapy and bone marrow transplantation in the treatment of cancer and lymphoma. CN1021592175A discloses a series of pharmaceutically acceptable salts of (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid.

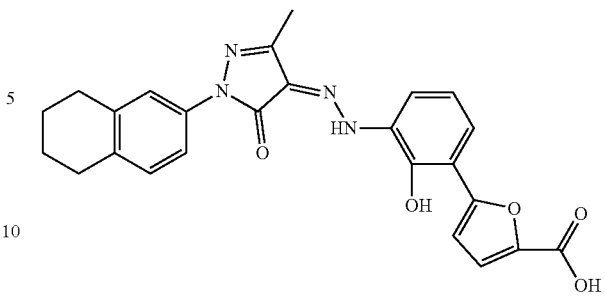

However, (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or a pharmaceutically acceptable salt thereof is unstable to moisture and heat. Especially, it has a poor thermal stability, and will be easily degraded. At the same time, due to the presence of various auxiliary materials, the degradation of compound A can be accelerated during the preparation of the drug. In addition, the composition formed with conventional pharmaceutical auxiliary materials is easy to absorb moisture, which will affect the dissolution rate and reduce the bioavailability in vivo. Therefore, it is a challenge for those skilled in the art to provide a formulation of (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid with a good stability, dissolution rate and bioavailability.

Direct tableting process is a simple, economical, rapid and new tablet production method, and has become a hot spot in the tableting field. The disadvantages of the conventional tablet production can be avoided: 1. The operation is complex; 2. It is not suitable for drugs that will be easily decomposed due to the addition of water, 3. It is not suitable for heat-sensitive drugs in the presence of heat drying process. However, direct tableting has higher requirements for the auxiliary materials, thus limited options. Most of the single auxiliary materials cannot meet the basic requirement for direct tableting, and multiple auxiliary materials are needed to work together.

Composite auxiliary material is a new auxiliary material that is obtained by evenly mixing two or more auxiliary materials in a proper proportion together through a certain process. It has a functional synergy and a uniform performance. At the same time, with the increased requirement of physical and chemical properties, safety and stability of new drugs, more and higher standards are set for the function of pharmaceutical auxiliary materials. The existing single auxiliary materials in the market cannot fully meet all the requirements. The development and application of composite auxiliary materials have become a trend in the field of pharmaceutical auxiliary materials.

SUMMARY OF THE INVENTION

The present invention provides a pharmaceutical composition comprising (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or a pharmaceutically acceptable salt thereof and a filler, wherein the filler is at least one selected from the group consisting of cellulose, microcrystalline cellulose, lactose and starch, preferably the filler is at least two selected from the group consisting of cellulose, microcrystalline cellulose, lactose and starch. The filler can be a composite auxiliary material that is prepared by premixing at least two selected from the group consisting of cellulose, microcrystalline cellulose, lactose and starch. The drug has a good compressibility and homogeneity, and its dissolution rate and bioavailability are excellent. In a preferred embodiment of the present invention, the dissolution test of the pharmaceutical composition is carried out according to the second method (paddle method) of the dissolution rate test described in the appendix of volume II of Chinese Pharmacopoeia 2010 Edition, using a pH 6.8 phosphate solution of 0.5% Tween 80 as a dissolution medium at 37±0.5° C. and at a paddle speed of 50 rpm, and the dissolution rate of the active drug is greater than 90% in 45 minutes, or greater than 94% in 60 minutes.

Furthermore, the filler of the present invention is preferably at least one selected from the group consisting of cellulose-lactose, microcrystalline cellulose-lactose, and lactose-microcrystalline cellulose-starch, more preferably cellulose-lactose and microcrystalline cellulose-lactose, and most preferably cellulose-lactose.

The composite auxiliary material described in the present invention can be obtained by physically mixing at least two pharmaceutical auxiliary materials in a certain weight ratio. The physical mixing includes wet granulation mixing, dry granulation mixing and hot melt extrusion mixing. After mixing, milling and sieving are carried out.

The "microcrystalline cellulose-lactose" in the present application refers to a spray-dried mixture of lactose and microcrystalline cellulose including, for example, a spray-dried mixture comprising about 75% by weight of lactose and about 25% by weight of microcrystalline cellulose. "Microcrystalline cellulose-lactose" can be Microcelac 100 sold by Meggle Company, but is not limited thereto.

The term "cellulose-lactose" in the present application refers to a spray-dried mixtures of lactose and powdered cellulose including, for example, a spray-dried mixture comprising about 75% by weight of lactose and about 25% by weight of powdered cellulose. "Cellulose-lactose" can be cellulose-lactose sold by Meggle Company (C80 for short) can be used as, but is not limited thereto.

The term "compressibility" in the present application is characterized by a compressibility index or a Hausner ratio. These two indexes are characteristic parameters characterizing powder compressibility. Compressibility index=(1−tap density/bulk density)×100%. Hausner ratio=bulk density/tap density.

The term "homogeneity" in the present application is measured according to content uniformity test. 10 tablets are used in the test, and the relative content X of each tablet with a labeled amount of 100 is measured respectively. The mean value X, standard deviation S, and absolute value A of the difference between the labeled amount and the mean value (|100−X|) are calculated. According to the Chinese Pharmacopoeia, if A+1.80S≤15.0, the content uniformity of the samples meets the requirement; if A+1.80S>15.0, the content uniformity of the samples does not meet the requirement. The term "RSD" in the present application refers to a relative standard deviation.

The method for determining the content uniformity of the pharmaceutical composition of the present invention is known to those skilled in the art. One tablet is placed into an appropriately sized measuring flask, and an appropriate amount of diluent (acetonitrile-water) is added. The mixture is shaken for 30 minutes to disintegrate, then placed under ultrasound for 2 minutes to dissolve. The mixture is cooled to room temperature, then diluted to the scale mark with the diluent, and shaken well. The mixture is centrifuged for 10 minutes (the speed is 10,000 rpm). The supernatant is taken and diluted with the diluent, and shaken well. 10 µl of the supernatant is precisely measured out, and injected into a liquid chromatograph instrument. The chromatogram is recorded, and the content is determined and should meet the requirement.

A powder with specific viscosity, certain flowability and compressibility can be prepared by mixing the composite auxiliary material of the present invention with other auxiliary materials in a specific ratio. The mixture has a controllable particle size, particle size distribution, and a certain viscosity after swelling with water. After the mixture is mixed with an active drug, granulation, tableting or direct tableting are carried out. The resulting tablets have a stable dissolution rate which meets the requirement.

The active ingredient of the present invention (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or a pharmaceutically acceptable salt thereof is present in an amount of 0.5-26%, and preferably 2.0-11% by weight, relative to the total weight of the pharmaceutical composition.

The filler of the present invention is present in an amount of 4-95%, preferably 60-92%, and more preferably 70-90% by weight, relative to the total weight of the pharmaceutical composition.

The pharmaceutical composition of the present invention also comprises a disintegrant, which can be selected from the group consisting of adipic acid, alginic acid, gelatinized starch, sodium carboxymethyl starch, carboxymethyl cellulose, calcium carboxymethyl cellulose, sodium carboxymethyl cellulose, hydrated silicon dioxide, calcium citrate, croscarmellose sodium, crospovidone, light anhydrous silicic acid, crystalline cellulose (microcrystalline cellulose), synthetic aluminum silicate, starch (which can be dry starch, wheat starch, rice starch, corn starch, potato starch, hydroxypropyl starch, pregelatinized starch, pregelatinized starch), cellulose acetate phthalate, calcium stearate, low-substituted hydroxypropyl cellulose, tragacanth powder, hydroxyethyl methyl cellulose, povidone, anhydrous citric acid, methyl cellulose, and calcium dihydrogen phosphate, and preferably a metallic element-free disintegrant. The metallic element of the present invention can be alkali metal, alkaline earth metal, or aluminum. The metallic disintegrant can be sodium carboxymethyl cellulose, sodium carboxymethyl starch, calcium citrate, croscarmellose sodium, synthetic aluminum silicate or calcium dihydrogen phosphate. That is to say, the disintegrant in the pharmaceutical composition of the present invention is preferably not these disintegrants containing a metal element.

The disintegrant of the present invention is further preferably at least one selected from the group consisting of dry starch, pregelatinized starch, adipic acid, alginic acid, hydrated silicon dioxide, cross-linked polyvinylpyrrolidone and low-substituted hydroxypropyl cellulose, more preferably at least one selected from the group consisting of pregelatinized starch and low-substituted hydroxypropyl cellulose. It can solve the problem of stability of the pharmaceutical composition when placed for a long time. At the same time, it can significantly reduce the hygroscopicity of the sample and facilitate storage. The resulting pharmaceutical composition has a good dissolution rate and bioavailability.

The disintegrant of the present invention is present in an amount of 5-30%, and preferably 8-20% by weight, relative to the total weight of the pharmaceutical composition.

The 90% particle size (D90 for short) of the active ingredient of the present invention (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or a pharmaceutically acceptable salt thereof is 10-100 μm, and preferably 10-50 μm, and/or the 50% particle size (D50 for short) is 1-20 μm, and preferably 3-20 μm. The active ingredient is readily mixed with the excipients. The resulting pharmaceutical composition can have a better in vitro dissolving behavior and content homogeneity. Such particle size can be obtained by the following method:

(Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or a pharmaceutically acceptable salt thereof with a large particle size is crushed by using a chopper, hammer mill, jet mill, cryogenic mill, airflow pulverizer and the like under a controlled temperature until the required particle size is obtained.

(Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or a pharmaceutically acceptable salt thereof with a large particle size can also be crushed with necessary auxiliary materials, thereby obtaining the required particle size meanwhile obtaining a more homogeneous pharmaceutical mixture.

The pharmaceutically acceptable salt of (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid of the present invention is selected from the group consisting of ethanolamine salt, choline salt, meglumine salt and tromethamine salt, and preferably diethanolamine salt (hereinafter referred to as compound B) that has the following structure:

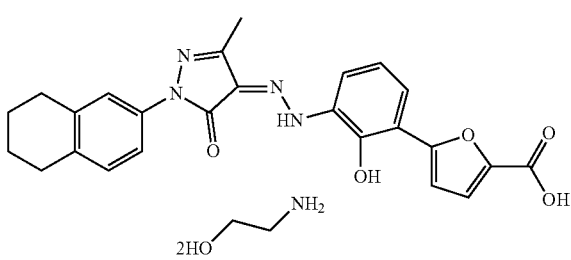

The pharmaceutical composition of the present invention can also comprise at least one excipient optionally selected from the group consisting of a binder, surfactant, glidant, and lubricant. The lubricant is that conventionally used in the art and can be selected from one or more of talc, magnesium stearate, zinc stearate, glyceryl behenate, hydrogenated vegetable oil, colloidal silicon dioxide, and stearic acid. Preferably, the lubricant is present in an amount of 0.5%-2% by weight, relative to the total weight of the pharmaceutical composition. The binder is that conventionally used in the art and can be selected from one or more of polyvinyl acetate resin, cellulose acetate phthalate, hydroxyethyl cellulose, hydroxyethyl methyl cellulose, hydroxypropyl cellulose, hydroxypropyl starch, hydroxypropyl methyl cellulose 2208, hydroxypropyl methyl cellulose 2906, hydroxypropyl methyl cellulose 2910, hydroxypropyl methyl cellulose phthalate, vinyl pyrrolidone-vinyl acetate copolymer, povidone, pregelatinized starch, and starch. Preferably, the binder is present in an amount of 2%-5% by weight, relative to the total weight of the pharmaceutical composition.

The glidant of the present invention is that conventionally used in the art and can be selected from the group consisting of hydrated silica (colloidal silicon dioxide), light anhydrous silicic acid, crystalline cellulose, synthetic aluminum silicate, titanium oxide, stearic acid, calcium stearate, magnesium stearate, tricalcium phosphate, talc, corn starch and magnesium aluminum silicate.

The surfactant of the present invention is that conventionally used in the art and can be selected from the group consisting of ionic surfactant and nonionic surfactant.

The ionic surfactant is stearic acid, sodium lauryl sulfate, lecithin, amino acids and the like; and the nonionic surfactant is glyceryl monostearate, polysorbate (Tween 80), fatty acid sorbitan, polyoxyethylene-polyoxypropylene copolymer (poloxamer), sodium lauryl sulfate and the like.

(Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or a pharmaceutically acceptable salt thereof used in the present invention can be obtained according to the methods disclosed in CN101679286A and CN1021592175A, or purchased commercially. The composite auxiliary material (or referred to as pre-mixed auxiliary material) with appropriate weight ratio and particle size can be prepared by the physical mixing method described above. The pre-mixed auxiliary material that meets the requirement, can also be purchased commercially, for example cellulose-lactose C80, Microcelac 100 and the like. Other conventional pharmaceutical auxiliary materials are purchased commercially.

DETAILED DESCRIPTION OF THE INVENTION

The present invention is further described in detail by the following examples and experimental examples. These examples and experimental examples are for illustrative purposes only, and are not intended to limit the scope of the present invention.

EXAMPLES 1 TO 6

Compound B, cellulose-lactose C80, low-substituted hydroxypropyl cellulose and magnesium stearate were weighted in a ratio shown in Table 1. Compound B, cellulose-lactose C80 and low-substituted hydroxypropyl cellulose were mixed well, then magnesium stearate was added and mixed well. The resulting materials were directly compressed into the desired tablets.

TABLE 1

| Components | Examples (mg/tablet) | | | | | |
|---|---|---|---|---|---|---|
| | 1 | 2 | 3 | 4 | 5 | 6 |
| Compound B | 3.17 | 3.17 | 6.33 | 6.33 | 25.33 | 63.32 |
| Cellulose-lactose C80 | 103.6 | 103.6 | 208.47 | 207.27 | 188.27 | 470.68 |
| Low-substituted hydroxypropyl cellulose | 12 | 18 | 24 | 24 | 24 | 60 |
| Magnesium stearate | 1.2 | 1.2 | 1.2 | 2.4 | 2.4 | 6.0 |
| Total | 120 | 120 | 240 | 240 | 240 | 600 |

EXPERIMENTAL EXAMPLE 1: DISSOLUTION TEST

Figure 1:
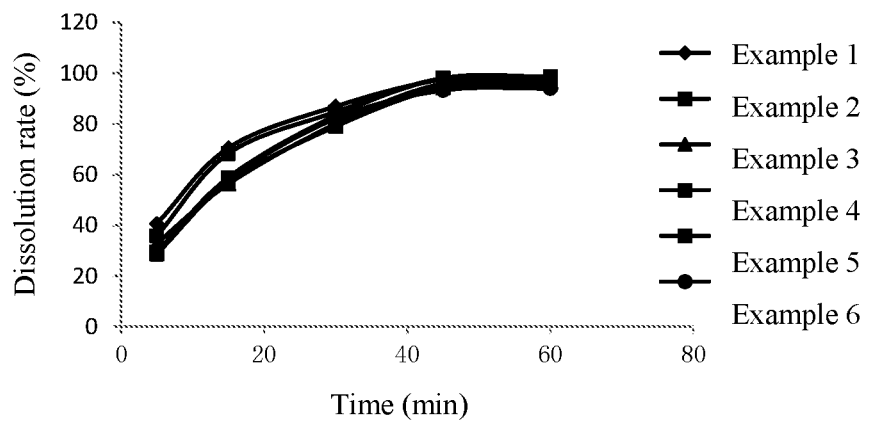
FIG. 1 shows the dissolution profiles of the tablets of Examples 1 to 6.

The dissolution rates of the tablets of Examples 1-6 were determined according to the second method (paddle method) of the dissolution rate test described in the appendix of volume II of Chinese Pharmacopoeia 2010 Edition. The dissolution test was carried out using a pH 6.8 phosphate solution of 0.5% Tween 80 (500 ml) as a dissolution medium at 37±0.5° C. and at a paddle speed of 50 rpm. The data in Table 2 shows that the dissolution rates of the drug were equal to or greater than 90% in 45 min, or equal to or greater than 94% in 60 min. The tablets thus have a good dissolution property, and the dissolution profiles are shown in FIG. 1.

TABLE 2

| Example 1 | | Example 3 | | Example 5 | | Example 2 | | Example 4 | | Example 6 | |
|---|---|---|---|---|---|---|---|---|---|---|---|
| Time min | Dissolution rate % | Time min | Dissolution rate % | Time min | Dissolution rate % | Time min | Dissolution rate % | Time min | Dissolution rate % | Time min | Dissolution rate % |
| 5 | 40.6 | 5 | 32.9 | 5 | 28.7 | 5 | 35.8 | 5 | 29.5 | 5 | 29.2 |
| 15 | 70.5 | 15 | 56.3 | 15 | 56.9 | 15 | 68.3 | 15 | 58.8 | 15 | 58 |
| 30 | 86.9 | 30 | 79.9 | 30 | 79 | 30 | 84.7 | 30 | 83.2 | 30 | 82.1 |
| 45 | 97.5 | 45 | 95.9 | 45 | 94.2 | 45 | 98.1 | 45 | 97.9 | 45 | 93.2 |
| 60 | 98.7 | 60 | 96.5 | 60 | 95.7 | 60 | 98.7 | 60 | 98 | 60 | 94 |

EXAMPLES 7 TO 8, COMPARATIVE EXAMPLES 1 TO 2

The compound was crushed respectively to obtain raw materials with different particle sizes, ready for use. Compound B with different particle sizes, cellulose-lactose C80, low-substituted hydroxypropyl cellulose and magnesium stearate were weighted in a ratio shown in Table 3. Compound B, cellulose-lactose C80 and low-substituted hydroxypropyl cellulose were mixed well, then magnesium stearate was added and mixed well. The resulting materials were directly compressed into the desired tablets.

TABLE 3

| Components | Comparative Example 1/mg | Comparative Example 2/mg | Example 7/mg | Example 8/mg |
|---|---|---|---|---|
| Particle size of compound B (μm) | D0.5 = 1.173<br>D0.9 = 2.380 | D0.5 = 2.726<br>D0.9 = 176.304 | D0.5 = 3.490<br>D0.9 = 20.667 | D0.5 = 9.751<br>D0.9 = 61.093 |
| Compound B | 6.33 | 6.33 | 6.33 | 25.33 |
| Cellulose-lactose C80 | 213.2 | 213.2 | 213.2 | 213.2 |
| Low-substituted hydroxypropyl cellulose | 19 | 19 | 19 | 19 |
| Magnesium stearate | 1.5 | 1.5 | 1.5 | 1.5 |
| Total | 240 | 240 | 240 | 240 |

EXPERIMENTAL EXAMPLE 2: DISSOLUTION TEST

Figure 2:
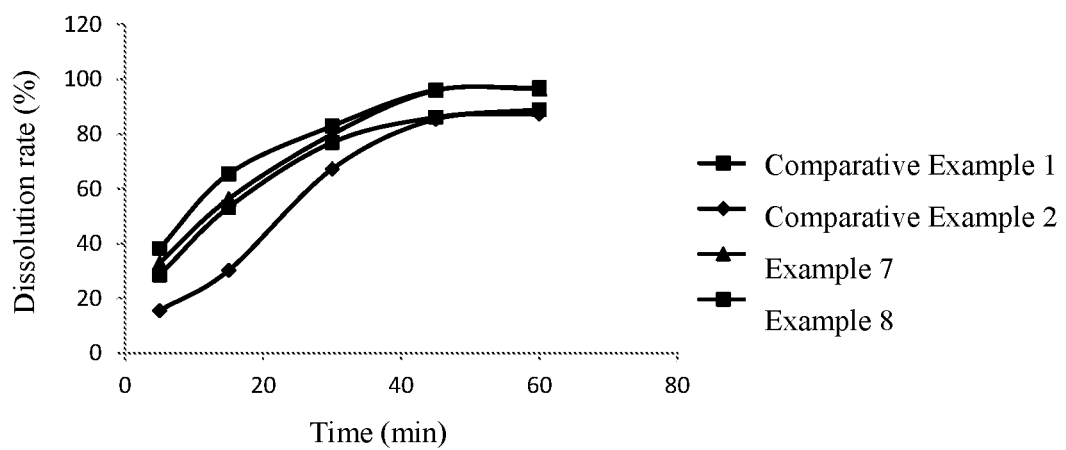
FIG. 2 shows the dissolution profiles of the tablets of Examples 7 to 8 and the tablets of Comparative Examples 1 to 2.

The dissolution rates of the tablets of Examples 7-8 and Comparative Examples 1 and 2 were determined according to the second method (paddle method) of the dissolution rate test described in the appendix of volume II of Chinese Pharmacopoeia 2010 Edition. The dissolution test was carried out using a pH 6.8 phosphate solution of 0.5% Tween 80 (500 ml) as a dissolution medium at 37±0.5° C. and at a paddle speed of 50 rpm. The data in Table 4 shows that the drug dissolution of the tablets of Examples 7-8 is rapid and complete; the drug dissolution rate of Comparative Example 1 is 86% in 45 min, and 90% in 60 min; the drug dissolution rate of Comparative Example 2 is 85.4% in 45 min, and 87.3% in 60 min; the dissolution of Comparative Examples 1 and 2 is incomplete, and the dissolution property is significantly inferior to that of Experiments 7 and 8. The dissolution profiles are shown in FIG. 2.

TABLE 4

| Comparative Example 1 | | Comparative Example 2 | | Example 7 | | Example 8 | |
|---|---|---|---|---|---|---|---|
| Time min | Dissolution rate % | Time Min | Dissolution rate % | Time min | Dissolution rate % | Time min | Dissolution rate % |
| 5 | 28.5 | 5 | 15.5 | 5 | 32.9 | 5 | 38.2 |
| 15 | 53.2 | 15 | 30.2 | 15 | 56.3 | 15 | 65.4 |
| 30 | 76.9 | 30 | 67.2 | 30 | 79.9 | 30 | 82.9 |
| 45 | 86.1 | 45 | 85.4 | 45 | 95.9 | 45 | 96.1 |
| 60 | 88.9 | 60 | 87.3 | 60 | 96.5 | 60 | 96.9 |

EXAMPLES 9-12, COMPARATIVE EXAMPLES 3 AND 4

Compound B, a filler (cellulose-lactose C80, lactose or microcrystalline cellulose and the like), low-substituted hydroxypropyl cellulose and magnesium stearate were weighted in a ratio shown in Table 5. Compound B, the filler and low-substituted hydroxypropyl cellulose were mixed well, then magnesium stearate was added and mixed well. The resulting materials were directly compressed into the desired tablets. The compressibility of the materials is shown in Table 6.

TABLE 5

| Components | Comparative Example 3/mg | Comparative Example 4/mg | Example 9/mg | Example 10/mg | Example 11/mg | Example 12/mg |
|---|---|---|---|---|---|---|
| Compound B | 6.33 | 6.33 | 6.33 | 6.33 | 6.33 | 6.33 |
| Cellulose-lactose C80 | 0 | 0 | 0 | 180 | 213 | 260 |
| Microcelac100 | 0 | 0 | 180 | 0 | 0 | 0 |
| Mannitol | 0 | 150 | 0 | 0 | 0 | 0 |
| Lactose | 150 | 0 | 0 | 0 | 0 | 0 |
| Microcrystalline cellulose | 63 | 63 | 33 | 33 | 0 | 0 |
| Low-substituted hydroxypropyl cellulose | 19 | 19 | 19 | 19 | 19 | 23 |
| Magnesium stearate | 1.5 | 1.5 | 1.5 | 1.5 | 1.5 | 1.8 |
| Total | 240 | 240 | 240 | 240 | 240 | 291 |

TABLE 6

| Index | Comparative Example 3/mg | Comparative Example 4/mg | Example 9/mg | Example 10/mg | Example 11/mg | Example 12/mg |
|---|---|---|---|---|---|---|
| Bulk density ($g*ml^{-1}$) | 0.356 | 0.355 | 0.351 | 0.355 | 0.358 | 0.351 |
| Tap density ($g*ml^{-1}$) | 0.440 | 0.444 | 0.449 | 0.448 | 0.450 | 0.459 |
| Compressibility index (%) | 23.6 | 20.0 | 27.9 | 26.2 | 25.7 | 30.8 |

As shown in Table 6, it is found during the preparation process of tablets that the material compressibility of Comparative Examples 2 and 3 (in which single auxiliary materials lactose, microcrystalline cellulose or mannitol is used as the filler) is inferior to that of Examples 9 to 12 (in which composite auxiliary materials were used).

TABLE 7

| Index | Comparative Example 3/mg | Comparative Example 4/mg | Example 9/mg | Example 10/mg | Example 11/mg | Example 12/mg |
|---|---|---|---|---|---|---|
| Average content | 98.87 | 100.21 | 98.91 | 100.13 | 99.81 | 99.71 |
| A + 1. 8S | 10.80 | 11.25 | 4.56 | 3.11 | 4.16 | 3.90 |
| RSD | 3.26 | 3.35 | 2.80 | 1.65 | 2.21 | 1.89 |
| Homogeneity | Moderate | Moderate | Good | Good | Good | Good |

As shown in Table 7, the content uniformity (or homogeneity) of drug in Comparative Examples 3 to 4 and Examples 9 to 12 was determined. The content homogeneity of drug (A+1.8S) in each Comparative Example and Example are all less than 15%. However, the RSD of Examples 9-12 is lower, indicating that the content homogeneity of drug is better when composite auxiliary material is used.

EXPERIMENTAL EXAMPLE 3: DISSOLUTION TEST

Figure 3:
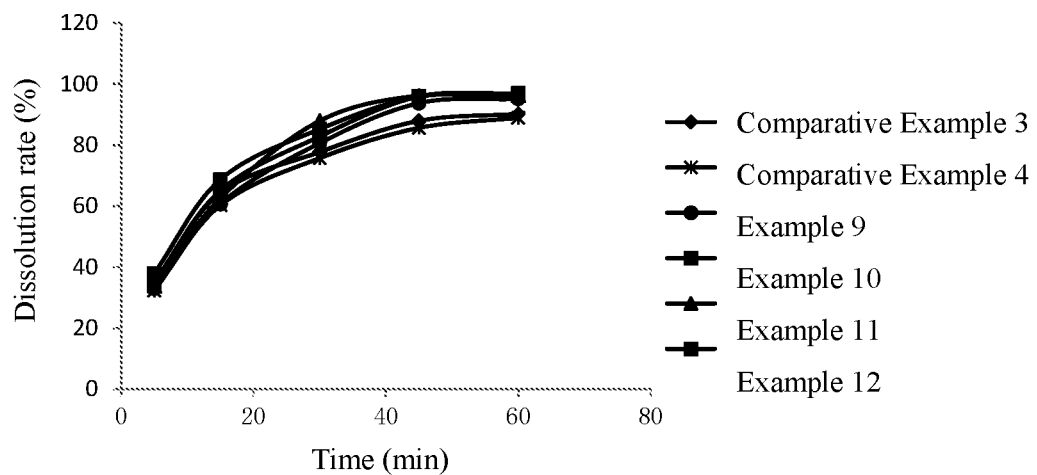
FIG. 3 shows the dissolution profiles of the tablets of Examples 9 to 12 and the tablets of Comparative Examples 3 to 4.

The dissolution rates of the tablets of Examples 9-12 and Comparative Examples 3 and 4 were determined according to the second method (paddle method) of the dissolution rate test described in the appendix of volume II of Chinese Pharmacopoeia 2010 Edition. The dissolution test was carried out using a pH 6.8 phosphate solution of 0.5% Tween 80 (500 ml) as a dissolution medium at 37±0.5° C. and at a paddle speed of 50 rpm. The data in Table 8 shows that, in the tablets of Examples 9-12 that comprise cellulose-lactose or Microcelac 100, the dissolution of compound B is rapid and complete, however in the tablets of Comparative Examples 3 and 4, the drug dissolution is slow and incomplete. The dissolution profiles are shown in FIG. 3.

TABLE 8

| Comparative Example 3 | | Comparative Example 4 | | Example 9 | | Example 10 | | Example 11 | | Example 12 | |
|---|---|---|---|---|---|---|---|---|---|---|---|
| Time min | Dissolution rate % | Time min | Dissolution rate % | Time min | Dissolution rate % | Time min | Dissolution rate % | Time min | Dissolution rate % | Time min | Dissolution rate % |
| 5 | 35.2 | 5 | 32.3 | 5 | 32.9 | 5 | 37.9 | 5 | 33.8 | 5 | 35.1 |
| 15 | 64.3 | 15 | 60.3 | 15 | 60.7 | 15 | 68.7 | 15 | 62.6 | 15 | 65.1 |
| 30 | 77.7 | 30 | 75.7 | 30 | 80.6 | 30 | 85.2 | 30 | 87.9 | 30 | 82.8 |
| 45 | 87.9 | 45 | 85.6 | 45 | 93.7 | 45 | 95.8 | 45 | 96.2 | 45 | 95.9 |
| 60 | 90.2 | 60 | 88.9 | 60 | 95.1 | 60 | 96.1 | 60 | 96.2 | 60 | 96.9 |

EXAMPLES 13-15, COMPARATIVE EXAMPLES 5-6

Compound B, cellulose-lactose C80, low-substituted hydroxypropyl cellulose or sodium carboxymethyl starch and magnesium stearate were weighted in a ratio shown in Table 9. Compound B, cellulose-lactose C80 and low-substituted hydroxypropyl cellulose or sodium carboxymethyl starch were mixed well, then magnesium was added stearate and mixed well. The resulting materials were directly compressed into the desired tablets. The compressibility of the materials is shown in Table 10.

TABLE 9

| Components | Comparative Example 5/mg | Comparative Example 6/mg | Example 13/mg | Example 14/mg | Example 15/mg |
|---|---|---|---|---|---|
| Compound B | 6.33 | 6.33 | 6.33 | 6.33 | 6.33 |
| Cellulose-lactose C80 | 213 | 213 | 220 | 213 | 196 |
| Low-substituted hydroxypropyl cellulose | 0 | 0 | 12 | 19 | 36 |
| Croscarmellose sodium | 0 | 19 | 0 | 0 | 0 |
| Sodium carboxymethyl starch | 19 | 0 | 0 | 0 | 0 |
| Magnesium stearate | 1.5 | 1.5 | 1.5 | 1.5 | 1.5 |
| Total | 240 | 240 | 240 | 240 | 240 |

TABLE 10

| Index | Comparative Example 5/mg | Comparative Example 6/mg | Example 13/mg | Example 14/mg | Example 15/mg |
|---|---|---|---|---|---|
| Bulk density (g*ml$^{-1}$) | 0.385 | 0.375 | 0.363 | 0.358 | 0.371 |
| Tap density (g*ml$^{-1}$) | 0.465 | 0.460 | 0.455 | 0.450 | 0.467 |
| Compressibility index (%) | 20.8 | 22.7 | 25.3 | 25.7 | 25.9 |

It is found during the preparation process of tablets that the compressibility of the material in which low-substituted hydroxypropyl cellulose is used as the disintegrant is superior to that of the material in which sodium carboxymethyl starch is used as the disintegrant.

EXPERIMENTAL EXAMPLE 4: DISSOLUTION TEST

Figure 4:
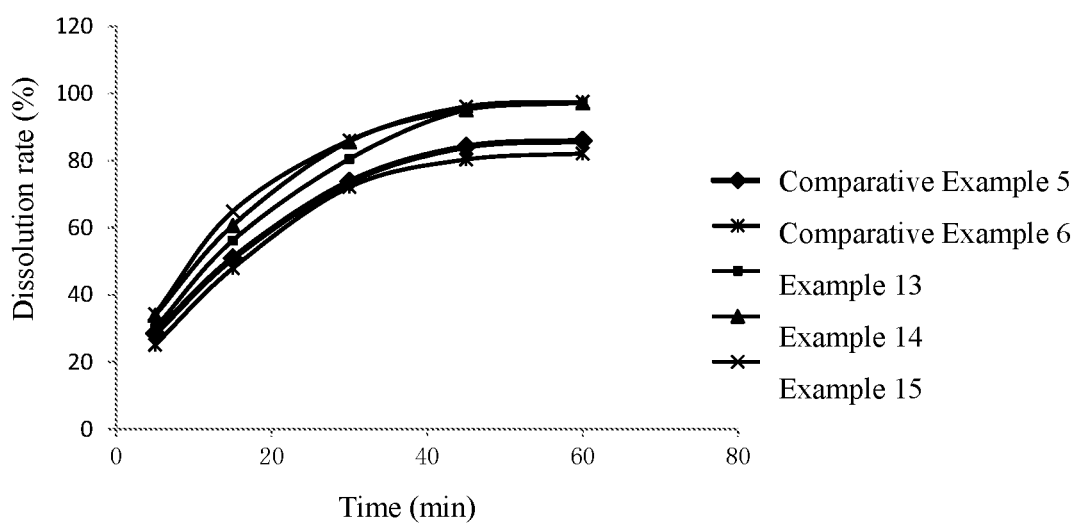
FIG. 4 shows the dissolution profiles of the tablets of Examples 13 to 15 and the tablets of Comparative Example 5.

The dissolution rates of the tablets of Examples 13-15 and Comparative Examples 5 to 6 were determined according to the second method (paddle method) of the dissolution rate test described in the appendix of volume II of Chinese Pharmacopoeia 2010 Edition. The dissolution test was carried out using a pH 6.8 phosphate solution of 0.5% Tween 80 (500 ml) as a dissolution medium at 37±0.5° C. and at a paddle speed of 50 rpm. The data in Table 11 shows that, in the tablets of Examples 13-15 that comprise low-substituted hydroxypropyl cellulose, the drug dissolution is rapid and complete, however in the tablets of Comparative Examples 5 to 6 that do not comprise low-substituted hydroxypropyl cellulose, the drug dissolution is slow and incomplete. The dissolution profiles are shown in FIG. 4.

TABLE 11

| Comparative Example 5 | | Comparative Example 6 | | Example 13 | | Example 14 | | Example 15 | |
|---|---|---|---|---|---|---|---|---|---|
| Time min | Dissolution rate % | Time min | Dissolution rate % | Time min | Dissolution rate % | Time min | Dissolution rate % | Time min | Dissolution rate % |
| 5 | 28.5 | 5 | 25.1 | 5 | 30.1 | 5 | 33.9 | 5 | 34.3 |
| 15 | 50.9 | 15 | 47.9 | 15 | 56.2 | 15 | 60.7 | 15 | 64.9 |
| 30 | 73.7 | 30 | 72.1 | 30 | 80.5 | 30 | 85.7 | 30 | 86 |
| 45 | 84.1 | 45 | 80.3 | 45 | 95.1 | 45 | 95.2 | 45 | 96.1 |
| 60 | 85.9 | 60 | 82.1 | 60 | 97.2 | 60 | 97.2 | 60 | 97.5 |

EXPERIMENTAL EXAMPLE 5: STABILITY TEST

The Compound B was mixed respectively with cellulose-lactose (cellactose 80), a simple mixture of cellulose and lactose (75%:25%), spray-dried lactose (Flowlac 100), microcrystalline cellulose PH302, or microcrystalline cellulose PH102 in a ratio of 1:10. The above mixtures and Compound B were placed respectively under conditions of 40° C./RH75%/open, 40° C./RH75%/closed, or 60° C./closed for 2 weeks and 4 weeks. The changes in appearance and related substances were observed, and the results are shown in Table 12.

TABLE 12

| Study Name | Study Conditions | Study Time | Appearance | Related substances (%) |
|---|---|---|---|---|
| Compound B | Initial point | 0 Day | Dark red powder | 0.90 |
| | 40° C./RH75%/open | 2 Weeks | Dark red mass | 1.32 |
| | | 4 Weeks | Dark red mass | 1.93 |
| | 40° C./RH75%/closed | 2 Weeks | Dark red powder | 1.08 |
| | | 4 Weeks | Dark red powder | 1.18 |
| | 60° C./closed | 2 Weeks | Dark red mass | 3.05 |
| | | 4 Weeks | Dark red mass | 4.84 |
| Compound B with microcrystalline cellulose PH302 | Initial point | 0 Day | Light brown powder | 0.92 |
| | 40° C./RH75%/open | 2 Weeks | Light brown powder | 1.52 |
| | | 4 Weeks | Light brown powder | 2.42 |
| | 40° C./RH75%/closed | 2 Weeks | Light brown powder | 1.09 |
| | | 4 Weeks | Light brown powder | 1.40 |
| | 60° C./closed | 2 Weeks | Khaki mass | 10.85 |
| | | 4 Weeks | Khaki mass | 15.26 |
| Compound B with microcrystalline cellulose PH102 | Initial point | 0 Day | Pink powder | 0.95 |
| | 40° C./RH75%/open | 2 Weeks | Pink powder | 1.71 |
| | | 4 Weeks | Pink powder | 2.36 |
| | 40° C./RH75%/closed | 2 Weeks | Pink powder | 1.10 |
| | | 4 Weeks | Pink powder | 1.22 |
| | 60° C./closed | 2 Weeks | Light khaki mass | 11.19 |
| | | 4 Weeks | Light khaki mass | 16.51 |
| Compound B with spray-dried lactose | Initial point | 0 Day | Light brown granule | 1.08 |
| | 40° C./RH75%/open | 2 Weeks | Light brown granule | 2.28 |
| | | 4 Weeks | Light brown granule | 4.13 |
| | 40° C./RH75%/closed | 2 Weeks | Light brown granule | 1.19 |
| | | 4 Weeks | Light brown granule | 1.22 |
| | 60° C./closed | 2 Weeks | Yellow-brown mass | 11.66 |
| | | 4 Weeks | Yellow-brown mass | 18.66 |
| Compound B with cellulose-lactose C80 | Initial point | 0 Day | Light brown granule | 1.08 |
| | 40° C./RH75%/open | 2 Weeks | Light brown granule | 1.51 |
| | | 4 Weeks | Light brown granule | 2.27 |
| | 40° C./RH75%/closed | 2 Weeks | Light brown granule | 1.24 |
| | | 4 Weeks | Light brown granule | 1.3 |
| | 60° C./closed | 2 Weeks | Light brown granule | 6.28 |
| | | 4 Weeks | Light brown granule | 11.77 |
| Compound B with a simple mixture of cellulose and lactose | Initial point | 0 Day | Light brown granule | 1.08 |
| | 40° C./RH75%/open | 2 Weeks | Light brown granule | 2.61 |
| | | 4 Weeks | Light brown granule | 4.45 |
| | 40° C./RH75%/closed | 2 Weeks | Light brown granule | 1.19 |
| | | 4 Weeks | Light brown granule | 1.22 |
| | 60° C./closed | 2 Weeks | Light brown granule | 7.66 |
| | | 4 Weeks | Light brown granule | 13.66 |

As can be seen from the data in the table, the mixture obtained by mixing compound B with the composite filler cellulose-lactose is more stable than the one obtained by mixing compound B with the simple mixture of cellulose and lactose, and is significantly more stable than the mixture obtained by mixing compound B with the single filler microcrystalline cellulose, lactose and the like.

What is claimed is:

1. A pharmaceutical composition, comprising (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl) furan-2-carboxylic acid or a pharmaceutically acceptable salt thereof, a disintegrant comprising low-substituted hydroxypropyl cellulose (L-HPC), and a filler, wherein the filler comprises at least one composite auxiliary material selected from the group consisting of cellulose-lactose, microcrystalline cellulose-lactose, and lactose-microcrystalline cellulose-starch.

2. The pharmaceutical composition according to claim 1, wherein the filler is present in an amount of 4-95% by weight, relative to the weight of the pharmaceutical composition.

3. The pharmaceutical composition according to claim 1, wherein the disintegrant is present in an amount of 5-30% by weight, relative to the total weight of the pharmaceutical composition.

4. The pharmaceutical composition according to claim 1, wherein the (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or the pharmaceutically acceptable salt thereof has a particle size D90 of 10-100 μm.

5. The pharmaceutical composition according to claim 1, wherein the (Z)-5-(2-hydroxy-3-(2-(3-methyl-5-oxo-1-(5,6, 7,8-tetrahydronaphthalen-2-yl)-1H-pyrazol-4(5H)-ylidene)hydrazino)phenyl)furan-2-carboxylic acid or the pharmaceutically acceptable salt thereof has a particle size D50 of 1-20 μm.

6. The pharmaceutical composition according to claim 1, comprising a pharmaceutically acceptable salt of (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid selected from the group consisting of an ethanolamine salt, a choline salt, a meglumine salt and a tromethamine salt.

7. The pharmaceutical composition according to claim 1, wherein the pharmaceutical composition further comprises at least one excipient selected from the group consisting of a binder, lubricant, surfactant, and glidant.

8. A method for preparing the pharmaceutical composition according to claim 1, comprising: a) mixing (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or a pharmaceutically acceptable salt thereof with a filler, a disintegrant and at least one excipient selected from the group consisting of a binder, lubricant, surfactant, and glidant to obtain a mixture; b) granulating the mixture obtained from step a) to obtain granules and then compressing the granules into a tablet, or directly compressing the mixture into a tablet.

9. The method according to claim 8, wherein the method further comprises mixing the granules obtained from step b) with a lubricant to prepare the tablet or fill a capsule.

10. The pharmaceutical composition according to claim 1, wherein the composite auxiliary material is selected from the group consisting of cellulose-lactose and microcrystalline cellulose-lactose.

11. The pharmaceutical composition according to claim 3, wherein the disintegrant is present in an amount of 8-20% by weight, relative to the total weight of the pharmaceutical composition.

12. The pharmaceutical composition according to claim 4, wherein the (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or the pharmaceutically acceptable salt thereof has a particle size D90 of 10-50 μm.

13. The pharmaceutical composition according to claim 5, wherein the (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid or the pharmaceutically acceptable salt thereof has a particle size D50 of 3-20 μm.

14. The pharmaceutical composition according to claim 6, comprising a diethanolamine salt of (Z)-5-(2-hydroxy-3-(2-(3-methyl-5-oxo-1-(5,6,7,8-tetrahydronaphthalen-2-yl)-1H-pyrazol-4(5H)-ylidene)hydrazino)phenyl)furan-2-carboxylic acid.

* * * * *